(12) United States Patent
Jia et al.

(10) Patent No.: US 10,426,331 B2
(45) Date of Patent: Oct. 1, 2019

(54) AUTOMATED QUANTIFICATION OF NONPERFUSION IN THE RETINA USING OPTICAL COHERENCE TOMOGRAPHY ANGIOGRAPHY

(71) Applicant: Oregon Health & Science University, Portland, OR (US)

(72) Inventors: Yali Jia, Portland, OR (US); David Huang, Portland, OR (US); Miao Zhang, Portland, OR (US)

(73) Assignee: Oregon Health & Science University

( * ) Notice: Subject to any disclaimer, the term of this patent is extended or adjusted under 35 U.S.C. 154(b) by 0 days.

(21) Appl. No.: 15/655,040

(22) Filed: Jul. 20, 2017

(65) Prior Publication Data
US 2018/0020909 A1    Jan. 25, 2018

Related U.S. Application Data

(60) Provisional application No. 62/364,788, filed on Jul. 20, 2016.

(51) Int. Cl.
| | |
|---|---|
| *A61B 3/00* | (2006.01) |
| *A61B 3/14* | (2006.01) |
| *A61B 3/12* | (2006.01) |
| *A61B 3/10* | (2006.01) |

(52) U.S. Cl.
CPC .......... *A61B 3/0025* (2013.01); *A61B 3/102* (2013.01); *A61B 3/1233* (2013.01); *A61B 3/14* (2013.01)

(58) Field of Classification Search
CPC .......... A61B 3/14; A61B 3/0025; A61B 3/12; A61B 3/102; A61B 3/0058

USPC .................................................... 351/206
See application file for complete search history.

(56) References Cited

U.S. PATENT DOCUMENTS

| | | | |
|---|---|---|---|
| 2011/0242306 A1* | 10/2011 | Bressler | A61B 3/12 348/78 |
| 2013/0301008 A1* | 11/2013 | Srivastava | G01B 9/02083 351/246 |
| 2016/0278627 A1* | 9/2016 | Huang | A61B 3/0025 |

* cited by examiner

*Primary Examiner* — Mohammed A Hasan
(74) *Attorney, Agent, or Firm* — Schwabe, Williamson & Wyatt, P.C.

(57) ABSTRACT

Disclosed are methods and systems for measuring areas of nonperfusion in the retina using OCT imaging. The disclosed methods and systems allow for the automated segmentation and quantification of avascular areas of the retina utilizing information obtained from both structural OCT and OCT angiography (OCTA) data. The disclosed methods include filtering approaches which enhance vessel structure while suppressing noise, dynamic thresholding approaches to mitigate the detrimental effects of within-scan variability and low scan quality, and distance transform-based approaches to improve detection of ischemic regions. When combined with methods such as projection-resolved OCTA, the sensitivity to detect nonperfusion within different plexuses of the inner retina is demonstrated. In the clinical setting of diabetic retinopathy, the disclosed methods and systems show high sensitivity and specificity to detect the mild non-proliferative form of the disease with high reproducibility.

37 Claims, 11 Drawing Sheets

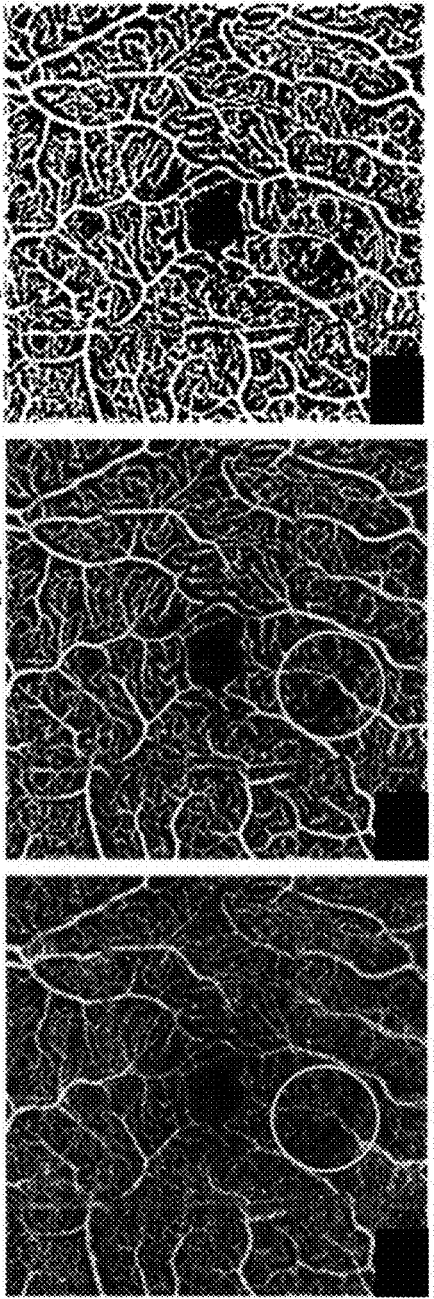
Figure 2A Original angiogram
Figure 2B Enhanced angiogram
Figure 2C Using fixed threshold
Figure 2D GCL+IPL reflectance image
Figure 2E Reflectance-adjusted threshold
Figure 2F Using Reflectance-adjusted threshold
Normal Figure 3A Original angiogram
Figure 3B Enhanced angiogram
Figure 3C Binary Vessel Mask
Figure 3D Vessel Distance Map

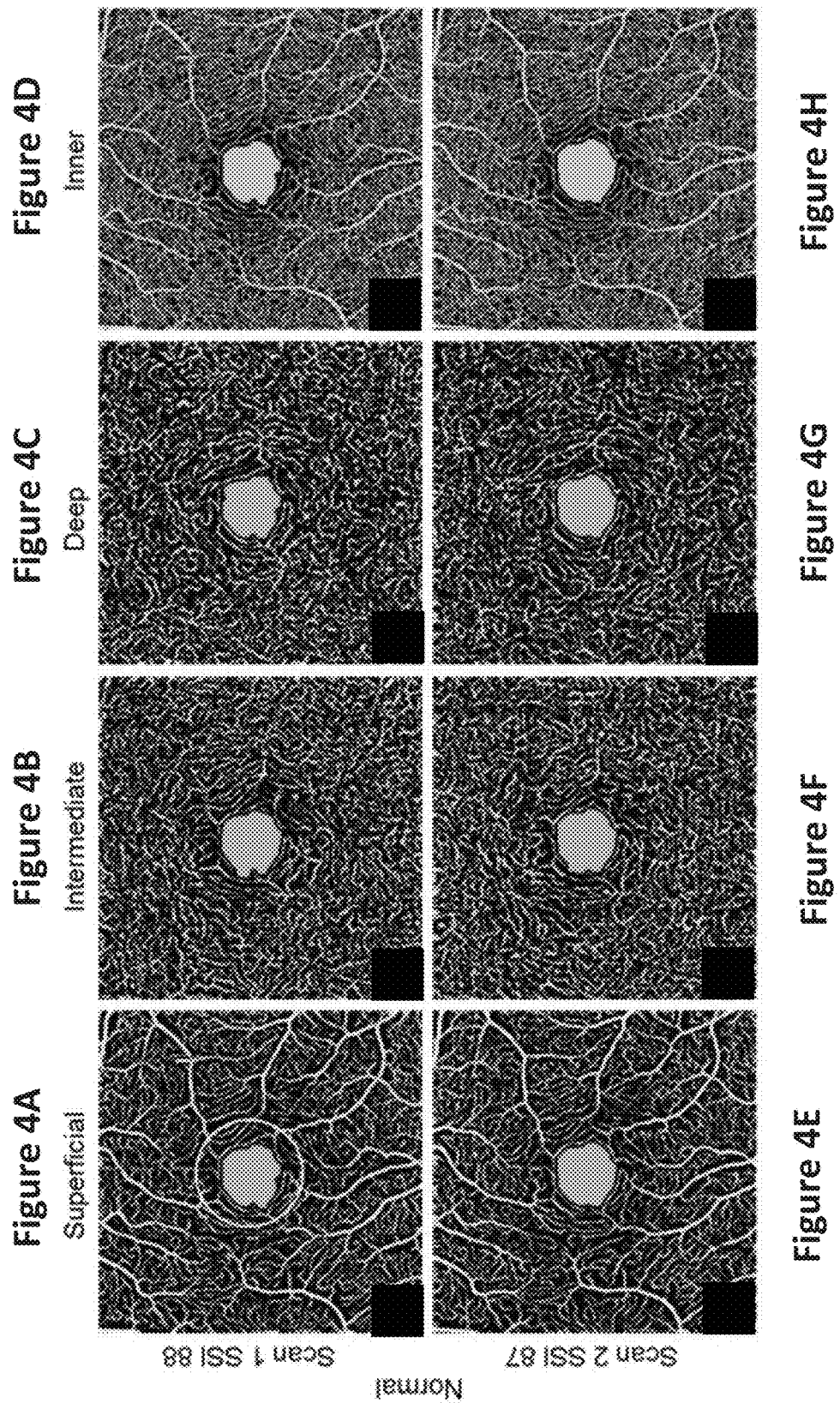

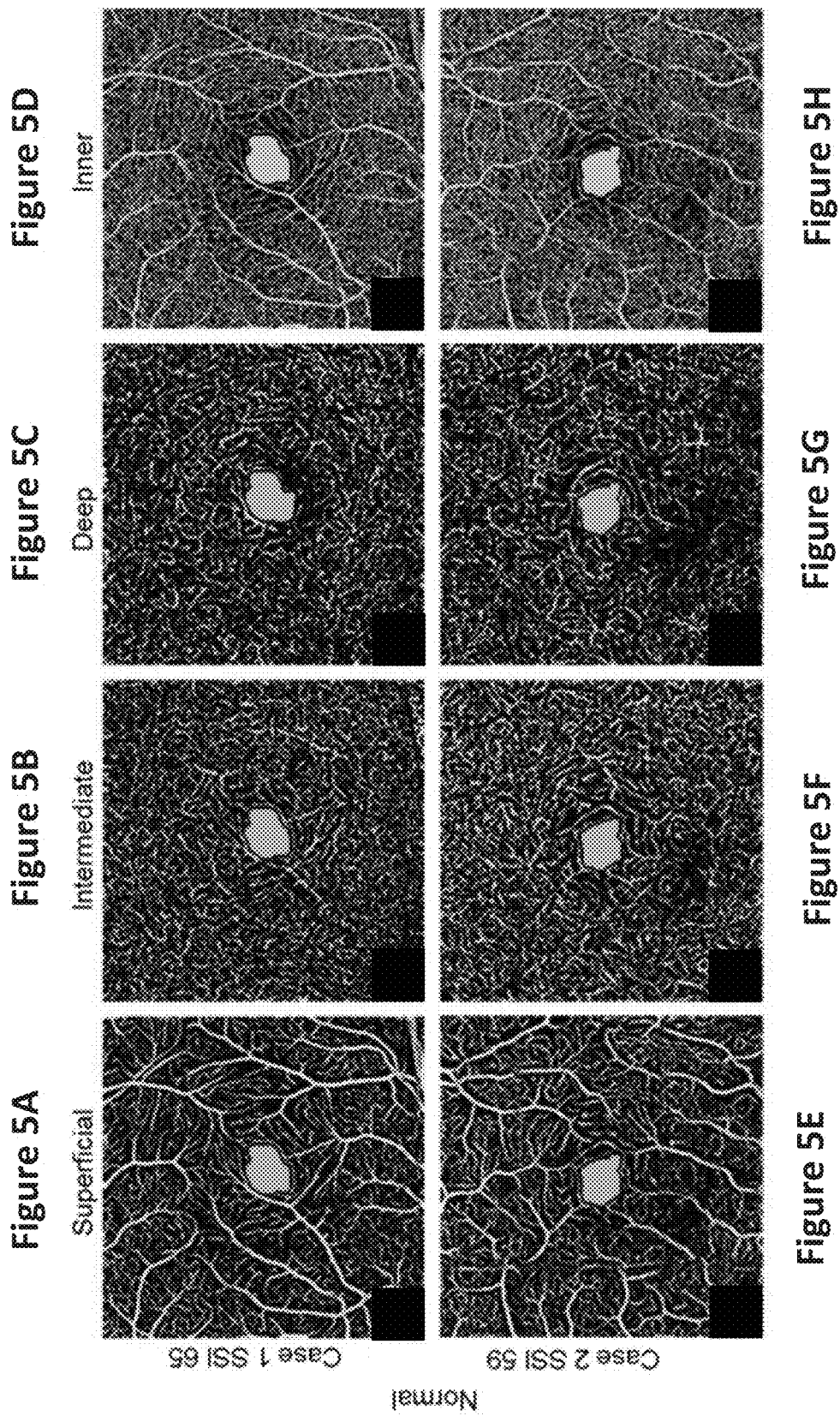

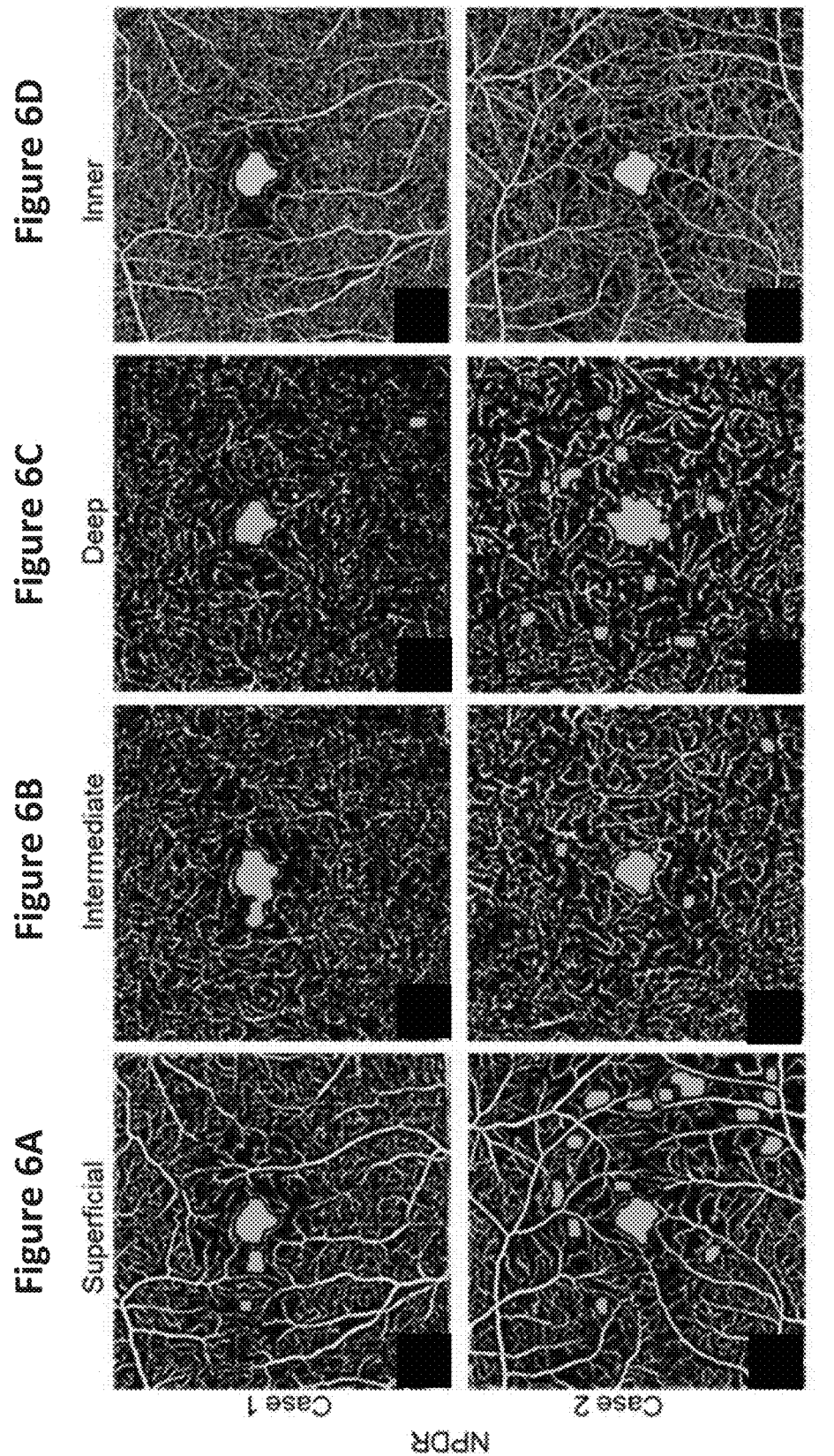

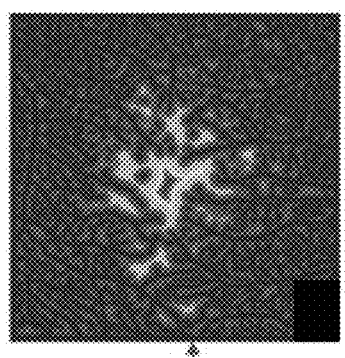
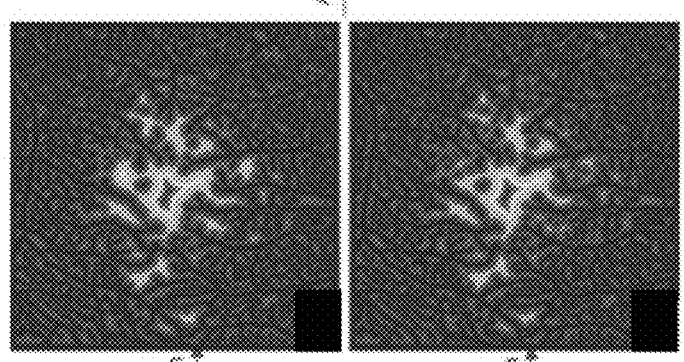
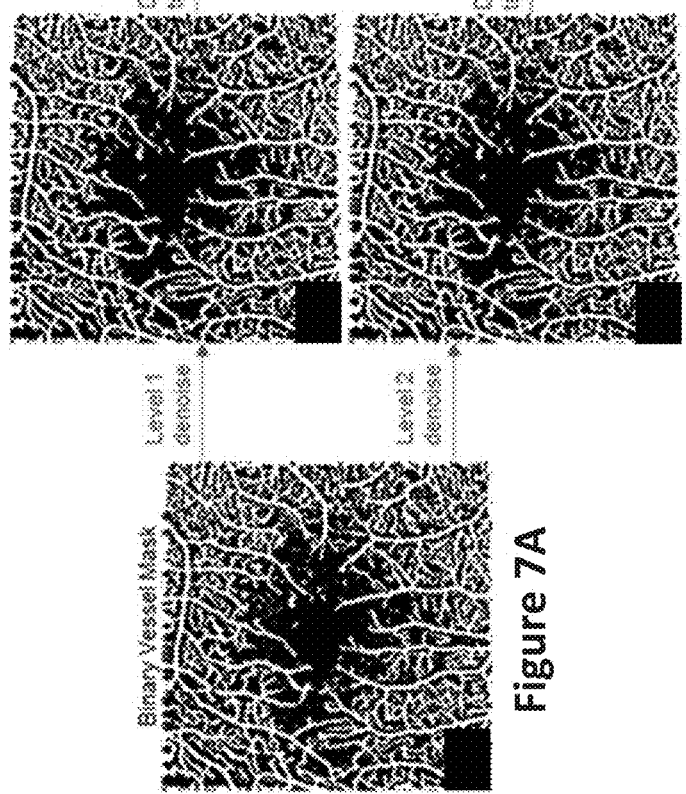

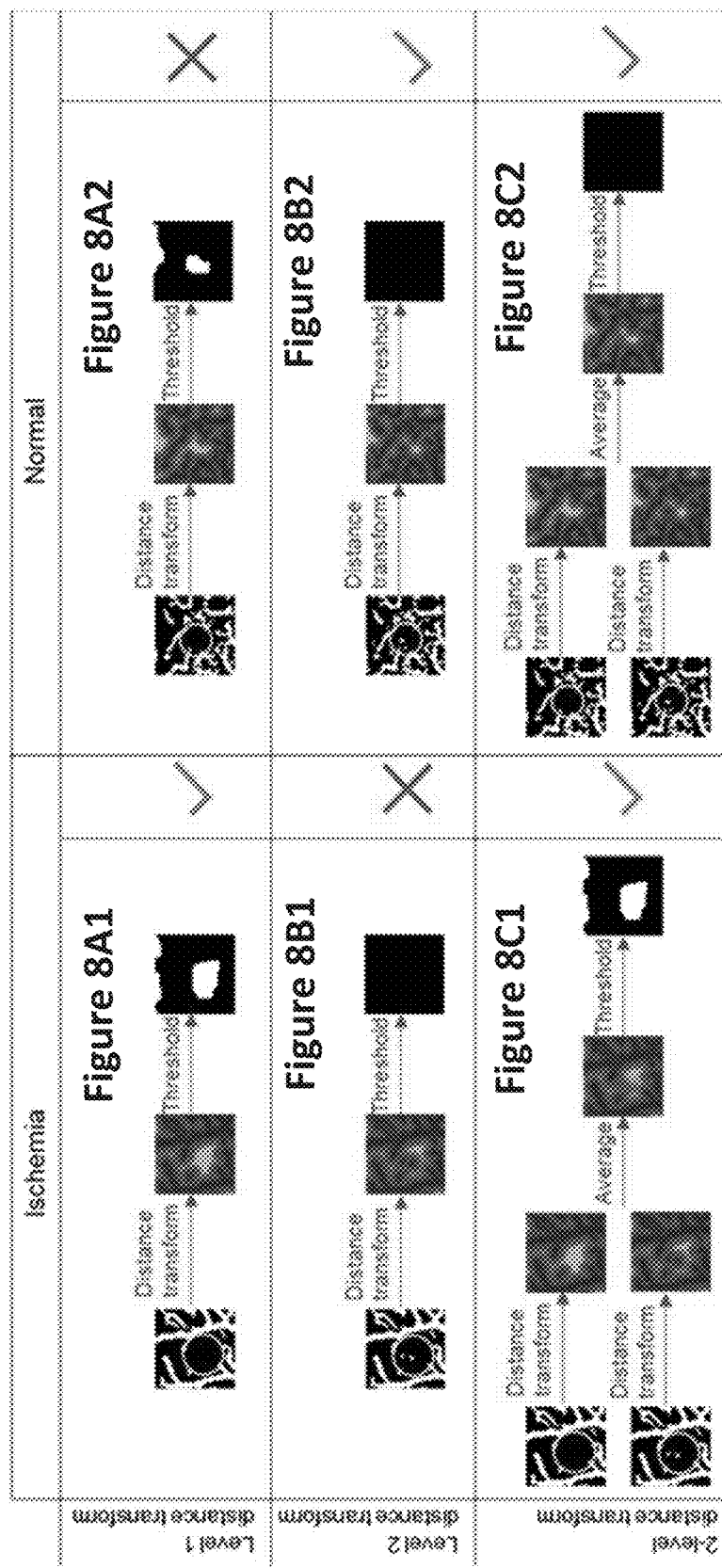

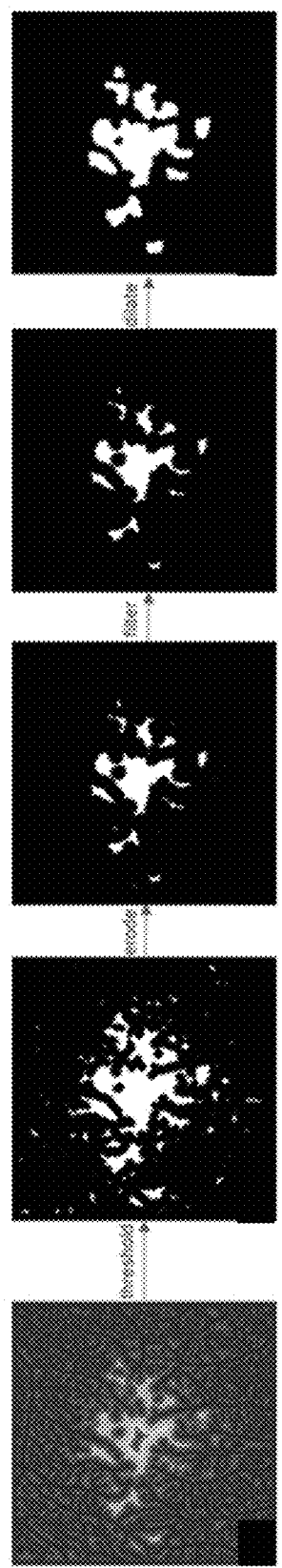

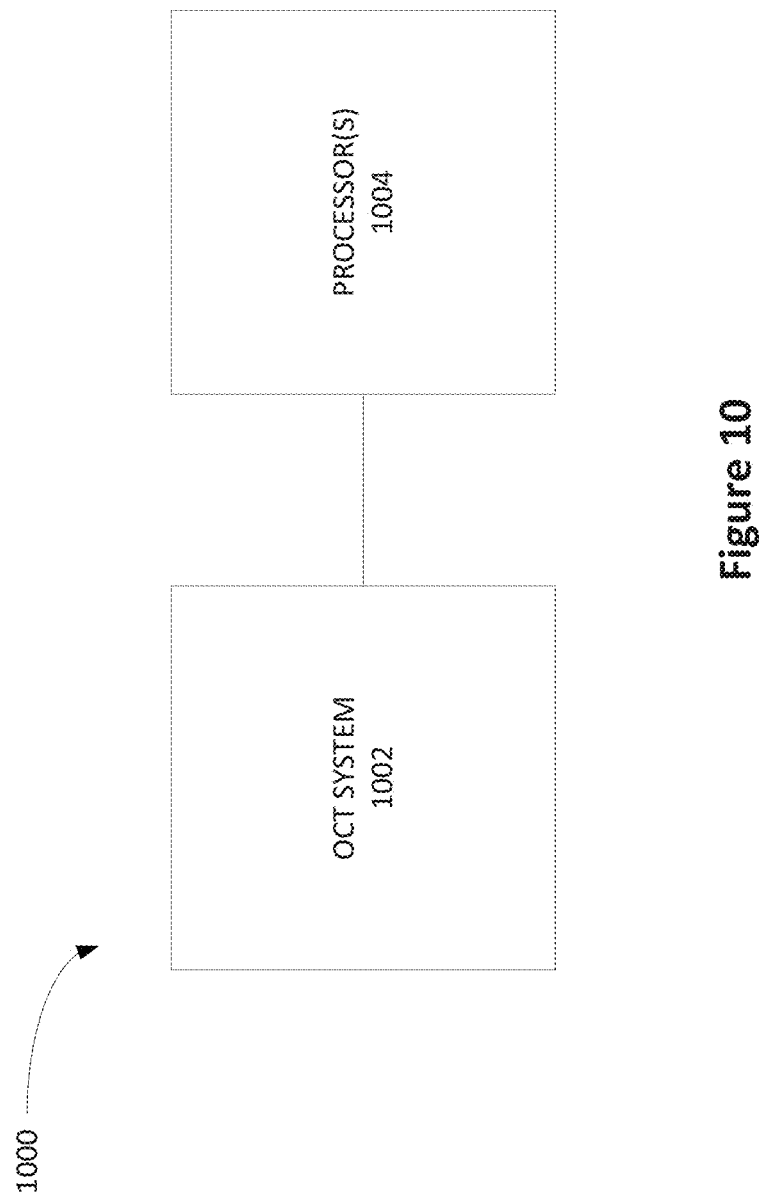

AUTOMATED QUANTIFICATION OF NONPERFUSION IN THE RETINA USING OPTICAL COHERENCE TOMOGRAPHY ANGIOGRAPHY

CROSS REFERENCE TO RELATED APPLICATION

The present application claims priority to U.S. Provisional Application No. 62/364,788, which was filed on Jul. 20, 2016, and titled "AUTOMATED QUANTIFICATION OF NONPERFUSION IN THE RETINA USING OPTICAL COHERENCE TOMOGRAPHY ANGIOGRAPHY," and which is hereby incorporated by reference herein.

ACKNOWLEDGEMENT OF GOVERNMENT SUPPORT

This invention was made with government support under EY023285, EY024544, and DK104397 awarded by National Institutes of Health. The government has certain rights in the invention.

FIELD

Generally, the field involves methods of imaging using optical coherence tomography. In particular, the field involves methods of visualizing areas of nonperfusion in the retina using optical coherence tomography angiography.

BACKGROUND

Diabetic retinopathy (DR) is characterized by capillary nonperfusion, vascular hyperpermeability, and neovascularization, and is a leading cause of blindness. Capillary nonperfusion, in particular, is an early indicator of DR and increases with severity of DR. The Early Treatment of Diabetic Retinopathy Study (ETDRS) qualitatively evaluated macular ischemia using fluorescein angiography (FA) and found it to have predictive value for progression of disease. Such rigorous grading of FA as used in the ETDRS study, however, is impractical for clinical practice. FA also suffers from several additional shortcomings, including dependence on early transit for macular capillary details, dye leakage which obscures of details of vascular structure, and variability of contrast. These limitations have hampered the clinicians' ability to assess nonperfusion objectively using FA. Thus, there remains an unmet need for an accurate, objective, and automated method to evaluate macular ischemia. Such a method would provide a valuable biomarker for DR with in-clinic applicability.

Optical coherence tomography angiography (OCTA) is an extension of structural optical coherence tomography (OCT) that can provide high-contrast imaging of capillary details without the need for dye injection. As such, OCTA provides a method to objectively evaluate capillary structure and health in a clinical setting. OCTA data can be used to automatically quantify total avascular area (AA) in the inner retina, and can detect DR with high sensitivity and specificity for patients having proliferative DR, the more advanced stage of the disease. However, detection of less severe forms of DR nonproliferative diabetic retinopathy (NPDR) remains a challenge. Part of the challenge is due to retinal anatomy: the inner retina is composed of three distinct, but tightly stacked, plexuses that are difficult to resolve into individual layers via OCTA because of projection artifacts. However, a new technique called Projection-resolved (PR) OCTA can be used to reduce the problem of projection artifacts blurring the plexuses together (e.g., as described in Zhang M, Hwang T S, Campbell J P, et al. Projection-resolved optical coherence tomographic angiography. Biomedical Optics Express 2016; 7:816-828, hereby incorporated by reference herein). Using PR-OCTA, individual plexuses revealed more areas of capillary drop out than seen in inner retinal angiograms of the plexuses. However, this increased sensitivity to detect capillary nonperfusion within individual plexuses is still susceptible to substantial noise artifacts. These noise artifacts degrade the integrity of imaged capillary structures and introduce spurious signal noise in non-capillary space, making quantification of AA less reliable and less reproducible. Thus, there remains a need for improved image processing methods to calculate AA in a robust and reliable manner.

BRIEF DESCRIPTION OF THE SEVERAL VIEWS OF THE DRAWINGS

FIGS. 2A-2F are a panel of six images showing the effect of using fixed versus reflectance-adjusted thresholding on a normal eye having a low signal strength region (marked by circle) caused by a vitreous opacity. The low signal region seen on the original angiogram in FIG. 2A persists with vesselness filter (shown in FIG. 2B) and binary filter with fixed threshold (shown in FIG. 2C), falsely simulating capillary drop out. FIG. 2D shows an en face map of ganglion cell layer (GCL) and inner plexiform layer (IPL) reflectance amplitude map, which is filtered and scaled to create the reflectance-adjusted threshold image shown in FIG. 2E. Using the reflectance-adjusted threshold image, the binary vessel mask (shown in FIG. 2F) does not show an area of false capillary drop out in the low reflectance area.

FIGS. 3A-3H are a panel of eight images showing an example of nonperfusion detection in the superficial plexus of a NPDR eye. The original angiogram (shown in FIG. 3A) is enhanced by a vesselness filter (shown in FIG. 3B) and processed with binary vessel mask with reflectance-adjusted thresholding (shown in FIG. 3C), which is used to create a vessel distance map (shown in FIG. 3D) by applying a distance transform. Morphologic operations are then used to remove regions with vessel distance less than 4 pixels (40 µm) (as shown in FIG. 3E), then eroded by a 5-pixel-wide square kernel and areas with minimum area smaller than 8 pixels or minor axis smaller than 2 pixels discarded (as shown in FIG. 3F). The remaining regions were dilated by 7-pixel-wide square kernel pixels (as shown in FIG. 3G). FIG. 3H shows the resulting avascular area (light blue) overlaid on the enhanced angiogram. It will be apparent that other embodiments may use other pixel/distance thresholds for the operations described above with respect to FIGS. 3A-3H.

FIGS. 4A-4H are a panel of eight images depicting the avascular area (AA) in two scans of a normal eye with high signal strength index (SSI), a measure of scan quality. The AA is limited to the foveal avascular zone and is similar in size and shape in all scans whether in individual plexuses or combined inner retinal angiogram. The extrafoveal AA (EAA) is defined as AA outside the white 1 mm circle (e.g., as shown in FIG. 4A).

FIGS. 5A-5H are a panel of eight images depicting the AA scans of two normal control eyes with relatively low signal strength index (SSI), a measure of scan quality. Scans in each of the three individual plexuses and the combined inner retinal angiogram are shown. No avascular area outside the foveal avascular zone is detected.

FIGS. 6A-6H are a panel of eight images depicting the AA in two eyes with mild NPDR. The three individual plexuses show incongruent areas of capillary nonperfusion that are not detected in the combined inner retinal angiogram.

FIGS. 7A, 7B1, 7B2, 7C1, 7C2, and 7D are a set of images showing an example of application of a two-level distance transform applied to a binary vessel mask. The original binary vessel mask (shown in FIG. 7A) was denoised at two different denoising levels (shown in FIGS. 7B1 and 7B2, respectively), then each distance transformed separately (shown in FIGS. 7C1 and 7C2, respectively), and the results averaged to generate a final vessel distance map (shown in FIG. 7D).

FIGS. 8A1, 8A2, 8B1, 8B2, 8C1, and 8C2 are a tabular presentation of example image processing operations that illustrate the advantage of using a two-level distance transform to detect nonperfusion area. Application of a level-1 distance transform correctly detects nonperfusion in ischemia (shown in FIG. 8A1) but falsely detects nonperfusion in a normal eye (shown in FIG. 8A2). Application of a level-2 distance transform correctly detects no areas of nonperfusion in the normal eye (shown in FIG. 8B2) but fails to detect nonperfusion in ischemia (shown in FIG. 8B1). Application of a two-level distance transform with averaging correctly characterizes both the ischemia (FIG. 8C1) and normal (FIG. 8C2) cases.

FIGS. 9A-9E are a set of images showing an example of thresholding and morphological operations applied to a distance map to produce a final detected nonperfusion region. FIG. 9A is a vessel distance map. FIG. 9B depicts an initial threshold of distance map. As shown in FIG. 9C, regions with vessel distance less than 4 pixels (40 μm) are eroded by a 5-pixel-wide square kernel. As shown in FIG. 9D, regions with minimum area smaller than 8 pixels or minor axis smaller than 2 pixels are discarded (i.e., filtered). As shown in FIG. 9E, remaining regions are dilated by 7-pixel-wide square kernel pixels, thereby generating the final detected nonperfusion region.

FIG. 10 schematically shows an example system for processing OCT and OCT angiography datasets to detect areas of nonperfusion in accordance with the disclosure.

DETAILED DESCRIPTION

Figure 1:
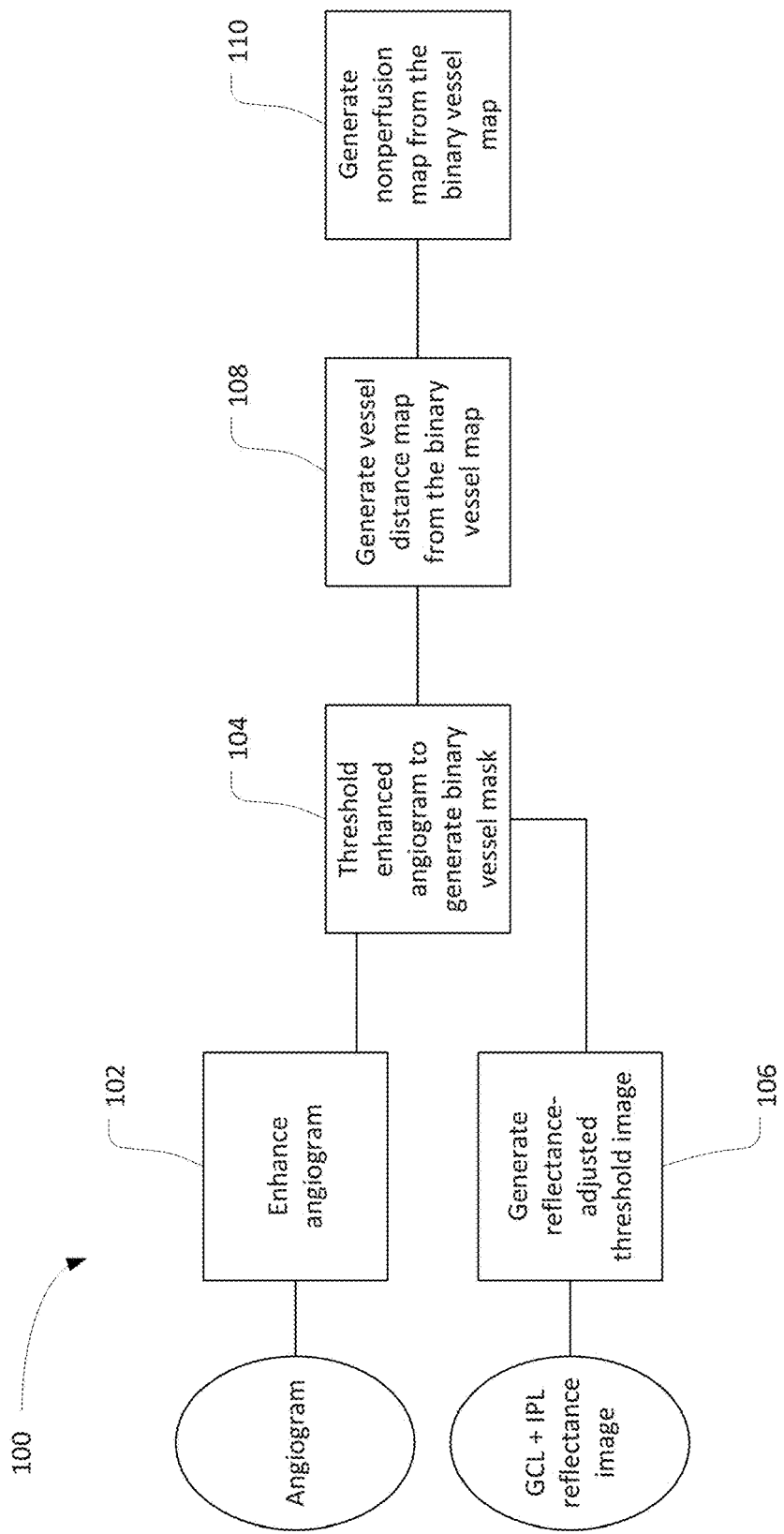
FIG. 1 is a flowchart showing an example method for quantification of capillary nonperfusion, in accordance with various embodiments.

Disclosed are methods and systems for identifying and measuring areas of nonperfusion in the retina. The disclosed methods and systems are applied to OCT angiograms derived from OCT angiography datasets. In embodiments, these OCT angiography datasets may be processed using projection-resolved OCTA (PR-OCTA) techniques to reduce shadowgraphic flow projection artifacts to improve resolution and quantification of vascular and avascular areas within different retinal layers.

The disclosed methods include filtering approaches that enhance the vascular structures present in an angiogram. This enhancement involves application of filter that maintains the vessel-like structure present in the angiogram image while also denoising (removing noise) the image to improve quantification. In embodiments, a "vesselness" filter based on eigenvalue analysis of the local microstructure within the angiogram is applied. In further embodiments, the vesselness filter can be applied at multiple scales to improve performance.

Also disclosed is a dynamic thresholding method that improves classification of flow pixels within an OCTA angiogram compared to fixed (i.e., constant) threshold approaches. In an embodiment disclosed herein, a reflectance-adjusted thresholding approach based on structural OCT images is presented that allows for dynamic or adaptive thresholding of angiogram images. In a disclosed embodiment, this approach produces an improved binary vessel mask segmentation for use in subsequent image processing operations. An aspect of reflectance-adjusted thresholding method is that it reduces sensitivity to overall scan quality, thereby improving quantification of vascular structure and nonperfusion area across multiple visits and scanning conditions. This approach also reduces sensitivity to within-visit variation due to locally reduced signals, which can be caused by, for example, vitreous opacity.

In an embodiment, a reflectance-adjusted thresholding image for use in dynamic thresholding can be produced by generating an en face reflectance image from structural OCT data, log-transforming the en face reflectance values, and applying a smoothing filter (for example, a Gaussian filter). The resultant image values may be further scaled and offset to generate a functional form of the reflectance-adjusted thresholding relationship. The scaling and offset constants of the functional form can be derived, in some embodiments, from a training set of angiogram images, wherein the training angiograms are generated using reflectance and flow data within specific layers of the retina. A maximum threshold may also be incorporated into the reflectance-adjusted thresholding image at the location of the foveal avascular zone (FAZ) to improve performance.

A further aspect of the disclosed methods is the use of a distance transform to calculate a vessel distance map from a binary vessel mask for use in quantifying avascular area. In an embodiment disclosed herein, a Euclidean distance transform is utilized. In a specific embodiment, a method for calculating a two-level vessel distance map is disclosed, wherein a binary vessel mask is denoised at two different levels and a distance transform applied to each to produce two vessel distance maps. These two vessel distance maps are then combined (for example, by averaging) to produce a single vessel distance map for use in characterizing nonperfusion area. An aspect of such a two-level vessel distance map is that it improves the sensitivity to detect ischemia in diseased eyes while maintaining a high specificity to avoid ischemia detection in healthy eyes.

Further disclosed are methods to modify the vessel distance map to improve its performance in mapping areas of nonperfusion. In an embodiment, the vessel distance map may be thresholded into a binary image and then subjected to morphological operations to remove spurious regions that arise from the threshold operation. As disclosed herein, such morphological operations may include erosion to pare the binary image, filtering to remove regions below a specified area or minor axis length, and/or dilation. The resultant improved vessel distance map can be used as a nonperfusion map to highlight the locations of avascular regions in the angiogram and calculate avascular area depicted in the original angiogram.

In a clinical study using the methods presented herein, the disclosed methods are shown to have high sensitivity (able to detect mild NPDR at 94.6% sensitivity with 96% specificity) and high reproducibility. It is also demonstrated that the methods are insensitive to scan quality.

Also disclosed herein is a system for measuring nonperfusion area using the disclosed methods. The system may include an OCT device configured to acquire OCT angiography data in functional connection with a computing device having a logic subsystem and data holding capabilities. In embodiments, the computing device receives data from the OCT device and performs one or more of the methods described herein.

In the present detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging based on the detection of spectral interference. Such imaging can be two-dimensional (2-D) or three-dimensional (3-D), depending on the application. Structural imaging can be of an extended depth range relative to prior methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction).

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value or a decorrelation value). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset of decorrelation values reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a 2D projection of the three-dimensional dataset onto a single planar image called an en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer could be used to generate an en face angiogram of the inner retina). Once generated, the en face angiogram image may be used to quantify various features of the retinal vasculature as described herein. This quantification typically involves the setting of a threshold value to differentiate, for example, the pixels that represent active vasculature from static tissue within the angiogram. These en face angiograms can be interpreted in a manner similar to traditional angiography techniques such as fluorescein angiography (FA) or indocyanine green (ICG) angiography, and are thus well-suited for clinical use. It is also common to generate en face images from structural OCT data in a manner analogous to that used to generate en face angiograms. Angiograms from different layers may also be color-coded and overlaid to present composite angiograms with encoded depth information; structural en face images may also be included in such composite image generation.

Disclosed herein is a method for automated quantification of retinal nonperfusion using OCTA in combination with several image processing techniques. In an embodiment, the disclosed method may be combined with the technique of projection-resolved OCT angiography (PR-OCTA) (e.g., as described in U.S. patent application Ser. No. 15/374,872, hereby incorporated by reference herein), to effectively detect areas of nonperfusion in distinct vessel networks that are normally difficult to resolve separately due to shadow-graphic projection artifacts. For example, as noted above, PR-OCTA allows the visualization of three distinct retinal plexuses and detection of capillary abnormalities not visible in inner retinal angiograms that combine these plexuses. However, even with PR-OCTA, the presence of noise artifacts within the acquired datasets introduces measurement errors that limits the reliable quantification of nonperfusion, and thus, limits the ability to distinguish patients with early or mild nonproliferative DR from normal patients.

In an example method disclosed herein, a noisy retinal angiogram containing blood flow information (e.g., decorrelation values) is filtered in such a way as to preserve the continuity capillary network structure in the image while also removing non-capillary noise. In an embodiment, a so-called "vesselness" filter may be used to enhance the inherent structure of the capillary network. In embodiments, a two-scale vesselness filter may be applied. Such a filter provides denoising of the angiogram while still enhancing both large vessels and capillaries. The denoising capability of such a filter serves to remove spurious pixels that can interfere with the detection of actual gaps between vessels, an important consideration in quantification of avascular area.

The resultant enhanced angiogram may further be segmented to create a binary vessel mask for use in quantifying capillary perfusion and identifying areas of nonperfusion. In an embodiment described herein, a reflectance-adjusted thresholding approach is disclosed to create such a binary vessel mask. In various embodiments, decorrelation values of the enhanced angiogram may be compared to a threshold and given a first binary value if they meet the threshold and a second binary value if they do not meet the threshold, thereby generating the binary vessel mask. The value of the threshold may be based on the local reflectance signal strength (e.g., for the given A-scan). The disclosed reflectance-adjusted approach reduces the sensitivity of the method to overall scan quality and to reflectance variations within a single scan. Such variations can be introduced, for example, by vitreous opacities which attenuate the optical signal and can falsely simulate capillary dropout. By using local reflectance signal strength as a reference for separating flow signal and background noise, false positive detection of nonperfusion is minimized and the repeatability of measurement improved.

The method may further employ a distance transform approach to process the binary vessel mask. In embodiments, the binary vessel mask may be denoised at multiple different levels (e.g., to remove different amounts of noise), and then a distance transform calculated for each of the multiple denoised masks to produce multiple distance maps. The resultant multiple distance maps may be combined, for instance by a weighted averaging approach, to produce a final distance map. An aspect of the distance transform is that it does not give disproportionate value to larger vessels. In addition, the use of the distance transform at multiple denoising levels overcomes the disadvantage that the distance transform can be sensitive to noise. Employing a multiple-level distance transform improves the sensitivity to ischemia while maintaining a high specificity to healthy subjects. In an embodiment described herein, application of a two-level distance map minimized disproportionate contribution of large vessels in determining vessel density abnormality and eliminated the undesirable detection of normal avascular area along large vessels of the superficial plexus as AA. In embodiments of the methods disclosed herein, morphologic operations may be applied to the calculated distance map to remove small regions while retaining larger regular shaped regions. Such morphological operations further reduce false positive detection of AA.

FIG. 1 shows a flowchart of an example implementation of a method 100 in accordance with embodiments described herein. The image processing strategy for quantification of nonperfusion area depicted in the flowchart is composed of three principal steps: (i) pre-processing; (ii) vessel distance transform; and (iii) morphological operations. These steps are described below using specific formulations of the image processing filters in an example workflow. It will be understood by one skilled in the art that other variations and formulations exist for the different aspects of the method 100.

(i) Pre-Processing

In an embodiment, at 102 of the method 100, an original angiogram (e.g., as shown in FIG. 2A and FIG. 3A) is enhanced using a vesselness filter. In some embodiments, the vesselness filter may be a two-scale vesselness filter, such as a two-scale ($\sigma$=1 and 2 pixels) Frangi vesselness filter. Example resultant images of an enhanced angiogram after application of the vesselness filter at 102 are shown in FIG. 2B and FIG. 3B. This filter may enhance vessels by obtaining a vesselness measure on the basis of eigenvalues of the second order local structure of the angiogram (Hessian) and suppresses background noise (e.g., as described in Fraz M M, Remagnino P, Hoppe A, et al. Blood vessel segmentation methodologies in retinal images: A survey. Computer Methods and Programs in Biomedicine 2013; 108:407-433; Sofka M, Stewart C V. Retinal Vessel Centerline Extraction Using Multiscale Matched Filters, Confidence and Edge Measures. IEEE Transactions on Medical Imaging 2006; 25:1531-1546; and/or Zhang H F, Maslov K, Li M-L, Stoica G, Wang L V. In vivo volumetric imaging of subcutaneous microvasculature by photoacoustic microscopy. Optics Express 2006; 14:9317-9323, each of which is hereby incorporated by reference herein).

At 104 of the method 100, the enhanced angiogram is thresholded to generate a binary vessel mask. The binary vessel mask may distinguish flow signal from the background noise. In some embodiments, a fixed (i.e., constant) threshold value may be used for the thresholding operation at 104. However, the flow noise floor depends on the OCT reflectance signal, which may vary among scans and even within a single scan. Consequently, with a fixed threshold cutoff, signal strength instability can cause within-visit variation leading to false detection of capillary dropout from locally reduced signal (e.g., local signal attenuation caused by vitreous opacity). An example of thresholding using a fixed threshold value is shown in FIG. 2C.

As an alternative to fixed value thresholding, a reflectance-adjusted threshold approach is disclosed that uses en face structural OCT of one or more reference layers (e.g., of the ganglion cell layer (GCL) and the inner plexiform layer (IPL)). The GCL and IPL retinal layers have moderate reflectance and are nearly free of cysts and exudates, making them good reference layers. In an embodiment, at 106 of the method 100, a reflectance-adjusted threshold image may be generated from a reflectance image (e.g., a GCL+ICL reflectance image). For example, the reflectance-adjusted threshold image may be generated by computing the mean projection of reflectance between the GCL and IPL layers (e.g., as shown in FIG. 2D), then taking the logarithm of those mean reflection values, and applying a smoothing filter. In a specific embodiment, the logarithm (S) of the mean projection is taken and filtered with a 15×15 pixels Gaussian operator G, having a standard deviation of 8 pixels, and then scaled. An example of the resultant reflectance-adjusted threshold image, $T_{xy}$, is shown in FIG. 2E. Mathematically, these operations may be represented by the following Equation (1):

$$T_{xy} = a \times G(S)_{xy} + b \quad (1)$$

The filter size and standard deviation in Equation 1 can be set empirically. The value a is a scaling parameter, and the value b is an offset parameter. The values a and b may be trained, for example, from scans having in-scan signal variation. In the examples presented herein, the scaling and offset parameters a and b, respectively, were trained using scans from two control eyes with in-scan signal variation and two NPDR eyes, identifying maximum capillary nonperfusion in NPDR while only identifying the foveal avascular zone (FAZ) in control eyes. The value of a was determined to be $8 \times 10^{-5}$ and b was $8 \times 10^{-2}$ for the specific images analyzed. A relatively high threshold (maximum of T) was assigned to 0.6 mm diameter central area to facilitate noise suppression in FAZ (see FIG. 2E). It should be noted that parameter values presented herein for the reflectance-adjusted thresholding are not intended to be limiting and one skilled in the art will understand the that they can be modified to achieve the desired image processing effects and to improve the quality of results.

As previously discussed, at 104 of the method 100, the reflectance-adjusted threshold image is compared with the enhanced angiogram to classify pixels as capillary or static tissue. The resultant image is a binary vessel mask by generated by adaptive (dynamic) thresholding of the angiogram. Example resultant binary vessel mask images are shown in FIG. 2F and FIG. 3C. The adaptive thresholding procedure can be expressed mathematically according to Equation (2):

$$B_{xy} = \begin{cases} 1, & \text{if } D_{xy} > T_{xy} \\ 0, & \text{if } D_{xy} < T_{xy} \end{cases} \quad (2)$$

where $B_{xy}$ is the binary vessel mask image, $D_{xy}$ is the enhanced angiogram (e.g., the decorrelation values of the enhanced angiogram at the corresponding x-y positions), and $T_{xy}$ is the reflectance-adjusted threshold image (e.g., the threshold values of the reflectance-adjusted threshold image at the corresponding x-y positions).

As shown in FIG. 2, false detection of capillary nonperfusion can be avoided by using the above-described reflectance-adjusted threshold approach (FIG. 2F) compared to fixed thresholding (FIG. 2C).

(ii) Vessel Distance Transform

At 108 of the method 100, the binary vessel mask obtained from the previous operations may be used to calculate a vessel distance map. The vessel distance map may be useful for characterizing the non-vessel space. In an embodiment, vessel distance map is calculated by applying a distance transform to the binary vessel mask image. In the examples presented herein, a Euclidean distance transform was applied to the binary vessel mask, and an example resultant vessel distance map is shown in FIG. 3D). The Euclidean distance transform of a binary image assigns a number that is the distance between that pixel and the nearest nonzero pixel of the binary image (e.g., as described in [34], hereby incorporated by reference herein), and may be calculated according to Equation (3):

$$DT_{xy} = \min_{B_{x'y'}=1} \sqrt{(x-x')^2 + (y-y')^2} \quad (3)$$

where $DT_{xy}$ is the distance transform, (x, y) is the given pixel of the binary vessel mask, (x', y') is the location of other pixels of the binary vessel mask (e.g., to identify the nearest vessel to the given pixel), and $B_{x'y'}=1$ corresponds to pixels of the binary vessel mask that have a value of 1 (to indicate a vessel). Thus, Equation (3) minimizes the value of $(x-x')^2 + (y-y')^2$ for values of (x', y') for which $B_{x'y'}=1$ to identify the nearest vessel to the given pixel. Accordingly, the values in the vessel distance map represent the distance of a given pixel (x, y) to its nearest vessel (x', y'). An advantage of the distance transform-based approach is that it does not give disproportionate value to larger vessels like the vessel density map, allowing more accurate detection of areas of capillary nonperfusion. In further embodiments, the image to which the distance transform is to be applied may be denoised prior to distance map calculation. Additionally, or alternatively, multiple distance maps can be calculated for an image which has been denoised at different levels, and the resultant maps combined. In the examples presented herein, the Euclidean distance transform is applied to a binary vessel mask that has been denoised at two different levels, and then results of the two maps averaged. This method ignores the normal avascular long-strip area along the large vessels, which is a commonly detected false positive region with simple thresholding methods.

(iii) Morphological Operations

Figures 3E, 3F, 3G, 3H:
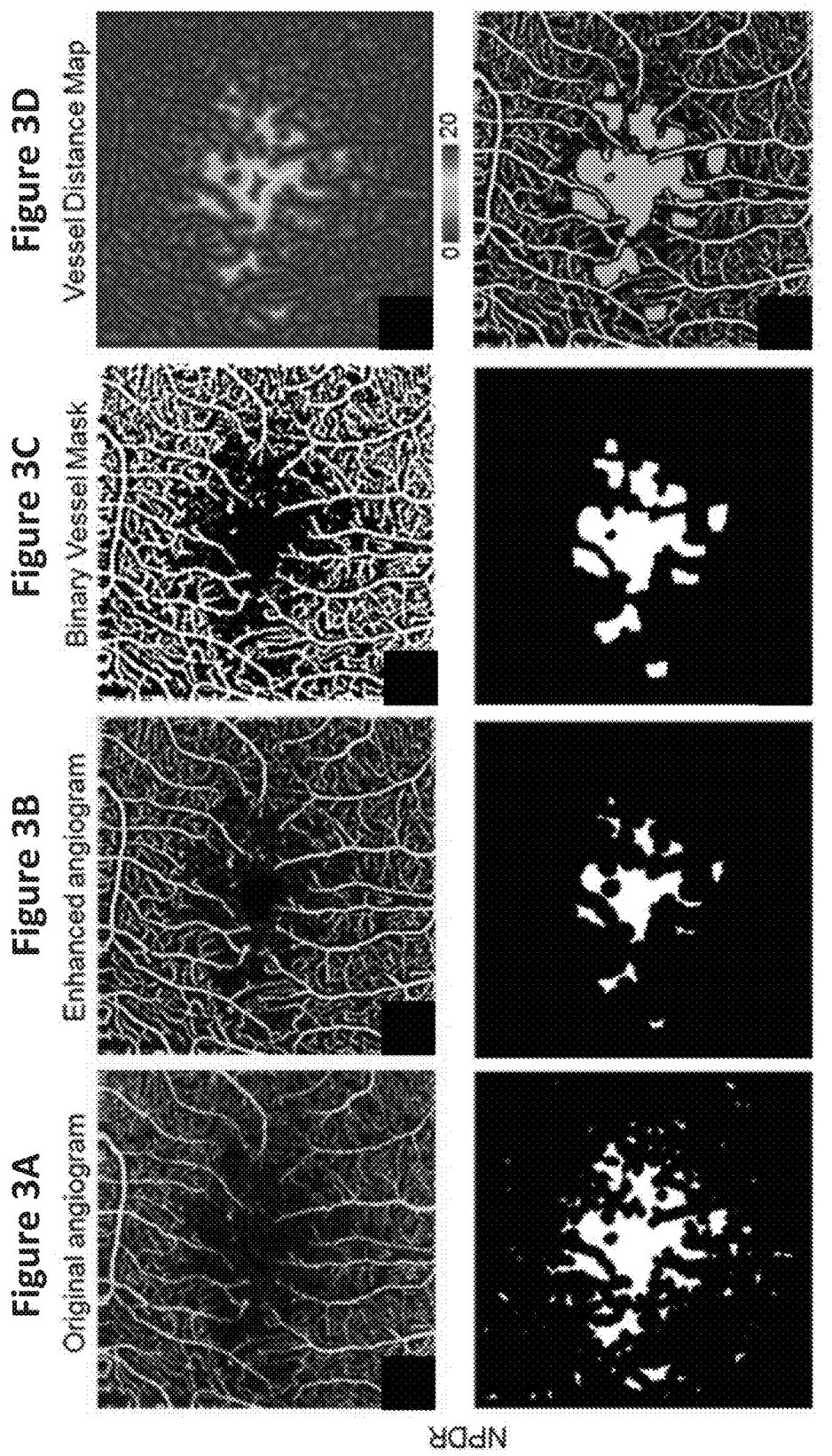

At 110 of the method 100, the nonperfusion map is generated from the vessel distance map. For example, the nonperfusion map may be generated by thresholding the vessel distance map and applying one or more morphological operations. In embodiments, the threshold level can be based on the statistical characteristics of the computed vessel distance map, or a value may be set empirically. In the examples presented herein, a threshold criterion of DT>4 was used, but this level may vary depending on application, as will be understood by one skilled in the art. FIG. 3E shows an example of a vessel distance map that has been thresholded at this DT>4 level. The morphological operations applied to the resultant thresholded distance map can include erosion, filtering, and dilation operations, as well as other appropriate processing techniques for processing images. For the examples presented herein, morphological operations include: (1) an erosion by 5-pixel-wide square kernel, (2) elimination of areas smaller than 8 pixels or whose minor axis length smaller than 2 pixels (FIG. 3F), (3) dilation by 7-pixel-wide square kernel (FIG. 3G). These operations and parameter values, however, are not intended to be limiting and one skilled in the art will understand the application of morphological operations to improve the quality of results. The final result of these morphological operations represent the final detection of nonperfusion regions in the angiogram. These results may be pseudo-colored and overlaid onto the original or enhanced angiogram to aid interpretation of results, for example, as shown in FIG. 3H.

The methods and operations described herein may be used to quantify AA, for example, in each of the three plexuses of the inner retina or in the total inner retinal angiogram encompassing all three plexuses. An advantage of the disclosed methods is that they limit detected AA to be relatively large, smooth contiguous areas and avoid detecting non-physiologic areas as AA.

EXAMPLES

Example 1—Detection of Mild NPDR

Data Acquisition

Healthy volunteers and diabetic participants with mild NPDR were recruited from Casey Eye Institute of Oregon Health and Science University (OHSU). Eyes with non-diabetic macular pathology, media opacity or other significant eye disease were excluded. An informed consent was obtained and the study was approved by the Institutional Review Board of OHSU. The study complied with the Declaration of Helsinki and Health Insurance Portability and Accountability Act. A clinical examination and masked-grading of 7-field color photographs confirmed the severity of retinopathy.

Two 3×3 mm scans with 2 mm depth were obtained in one eye of each participants within a visit using a commercial spectral domain OCT system (RTVue-XR; Optovue, Fremont, Calif.) with a center wavelength 840 nm, a full-width half maximum bandwidth of 45 nm, and an axial scan rate of 70 kHz. In the fast transverse scanning direction, 304 axial scans were sampled to obtain a single 3 mm B-scan. Two repeated B-scans were captured at a fixed position before proceeding to the next location. A total of 304 locations along a 3 mm distance in the slow transverse direction were sampled to form a 3D data cube. All 608 B-scans in each data cube were acquired in 2.9 seconds. Based on the volumetric OCT reflectance signal, the scanning software computed a signal strength index (SSI), which is often used as an indicator of scan quality.

Data Processing

Blood flow was detected using the split-spectrum amplitude decorrelation (SSADA) (e.g., as described in Jia Y, Tan O, Tokayer J, et al. Split-spectrum amplitude-decorrelation angiography with optical coherence tomography. Optics Express 2012; 20:4710-4725; Gao S S, Liu G, Huang D, Jia Y. Optimization of the split-spectrum amplitude-decorrelation angiography algorithm on a spectral optical coherence tomography system. Optics Letters 2015; 40:2305-2308; and/or Liu L, Jia Y, Takusagawa H L, et al. Optical coherence tomography angiography of the peripapillary retina in glaucoma. JAMA Ophthalmology 2015, each of which is hereby incorporated by reference herein). Projection artifacts were suppressed by a projection-resolved OCTA (PR-OCTA) algorithm (e.g., as described in Zhang M, Hwang T S, Campbell J P, et al. Projection-resolved optical coherence tomographic angiography. Biomedical Optics Express 2016; 7:816-828, hereby incorporated by reference herein). OCT structural images were obtained by averaging two repeated B-scans. The structural and angiography data were generated simultaneously on each scan. For each scan, one x-fast scan and one y-fast scan were registered and merged through an orthogonal registration algorithm to remove motion artifacts (e.g., as described in Kraus M F, Potsaid B, Mayer M A, et al. Motion correction in optical coherence tomography volumes on a per A-scan basis using orthogonal scan patterns. Biomedical Optics Express 2012; 3:1182-1199; and/or Kraus M F, Liu J J, Schottenhamml J, et al. Quantitative 3D-OCT motion correction with tilt and illumination correction, robust similarity measure and regularization. Biomedical Optics Express 2014; 5:2591-2613, both of which are hereby incorporated by reference herein).

A directional graph search algorithm identified structural boundaries (e.g., as described in Zhang M, Wang J, Pechauer A D, et al. Advanced image processing for optical coherence tomographic angiography of macular diseases. Biomedical Optics Express 2015; 6:4661-4675, hereby incorporated by reference herein): the inner limiting membrane (ILM), inner plexiform layer (IPL), inner nuclear layer (INL), outer plexiform layer (OPL), outer nuclear layer (ONL). The superficial plexus was defined as the slab within the inner 80% of GCC and minimum thickness of 61 microns. The intermediate plexus was defined as vessels in the outer 20% of GCC and inner 50% of INL. The deep plexus was defined as vessels in the remaining slab internal to the OPL and minimum thickness of 37 microns. A proportional rather than fixed segmentation scheme was chosen because the three plexuses merge at the edge of the foveal avascular zone (FAZ) and a fixed segmentation scheme can result in arbitrary and meaningless differences in FAZ size between the vascular plexuses. In the normal eye, this scheme shows each plexus reaching the edge of the FAZ and avoids differences in the measurement of FAZ of three plexuses caused by solely by the segmentation method.

These three plexuses have been well characterized histologically in non-human primates and recently in human cadaveric eyes. An en face OCT of each plexus was generated using maximum decorrelation projection of each slab. A combined angiogram showing the more superficial plexuses placed on top with different color showed the relationship between the plexuses.

The total AA (TAA) and the extrafoveal AA (EAA), defined as the AA outside the 1 mm central circle were separately tabulated. These values were corrected for magnification variation associated with axial length variation (e.g., as described in Huang D, Chopra V, Lu A T-H, Tan O, Francis B, Varma R. Does Optic Nerve Head Size Variation Affect Circumpapillary Retinal Nerve Fiber Layer Thickness Measurement by Optical Coherence Tomography? Disc Size and RNFL Layer Thickness Measurement by OCT. Investigative Ophthalmology & Visual Science 2012; 53:4990-4997, hereby incorporated by reference herein).

Data Analysis

The Mann-Whitney test was used to compare the detected AA between the patients with NPDR and the healthy controls. The diagnostic accuracy of each parameter was assessed by sensitivity with a fixed specificity and the area under the receiver operating characteristic curve (AROC). Repeatability of the detected AA was assessed by evaluating the pooled standard deviation (SD) for eyes that had two scans with a signal strength index (SSI) greater than 54. We also compared the detected AA in different plexuses in NPDR. All statistical tests were done using SPSS, version 20 (IBM).

The AA in healthy controls identified by the automated procedure was compared with manual grading for detection accuracy. The manual results were delineated by using the free selection tool in GIMP 2.8. The Jaccard coefficient, defined as the area of intersection divided by the area of union, measured the similarity between the automated result and manual result. The false positive and negative errors were also computed.

Results

Eyes from 13 healthy volunteers (mean [SD] age: 43[13], 10 women) and 13 participants with mild NPDR (mean [SD] age: 59[8], 7 women) were imaged and one eye from each participant was randomly chosen for inclusion in the study. The SSI of the control group ranged 59-88 and the NPDR group 54-81. No eye in the study had cysts in the inner retina. In the control group, the automated algorithm detected AA only inside the central 1 mm circle in combined 1-layer or 3-layer angiograms (FIG. 4) with the exception of one eye that had an extrafoveal AA of 0.01 mm². The AA in normal controls detected by automated algorithm agreed with manual grading with a Jaccard indices 0.85, 0.82, 0.81 for superficial, intermediate, and deep angiograms, respectively (Table 3) and was independent of signal strength variation between or within scans (FIG. 5).

In the NPDR group, the automated algorithm identified AA that were frequently incongruent between the three plexuses. As a result, it sometimes failed to detect any AA outside the FAZ when applied to combined inner retinal angiogram in eyes with AA in individual plexuses (FIG. 6). AA in the superficial and deep plexuses tended to be larger than in the intermediate plexus (Table 1).

There was no significant difference in EAA or TAA between the control and NPDR groups when the algorithm was applied to the combined 1-layer angiogram. When three plexuses were individually evaluated, the EAA and TAA in each of the three plexuses were significantly larger in the NPDR group compared to the control group (Table 1).

Holding the specificity at 95%, the 3-plexus showed that the sum of EAA was the most sensitive with the best diagnostic accuracy at AROC of 0.99 (Table 1). TAA had lower sensitivity and diagnostic accuracy.

Within-visit repeatability was assessed using eyes with 2 scans in the same visit with SSI greater than 54 (Table 2). 22 eyes from control participants and 17 eyes of NPDR participants had 2 scans with adequate signal strength. The pooled SD of AA ranged from 0.000 to 0.024 $mm^2$ in control and from 0.035 to 0.051 $mm^2$ in NPDR (Table 2). For all parameters, the pooled SD were smaller than the population SD or the difference between the NPDR and control group for parameter with a statistical difference between the groups (Table1).

TABLE 2

Within-visit repeatability of avascular area measurements

| | | Pooled SD ($mm^2$) | |
|---|---|---|---|
| Plexus | ROI | Control (n = 22[a]) | NPDR (n = 17[b]) |
| Superficial | EAA | 0.000 | 0.035 |
| | TAA | 0.008 | 0.042 |
| Intermediate | EAA | 0.000 | 0.007 |
| | TAA | 0.007 | 0.016 |
| Deep | EAA | 0.009 | 0.050 |
| | TAA | 0.011 | 0.077 |
| Total in 3 plexuses | EAA | 0.004 | 0.036 |
| | TAA | 0.024 | 0.051 |

ROI, region of interest;
SD, standard deviation;
NPDR, non-proliferative diabetic retinopathy;
EAA, extrafoveal avascular area outside the central 1 mm circle;
TAA, total avascular area in the whole scan.

TABLE 3

Agreement between automated detection and manual delineation of the macular avascular area in normal controls

| Plexus | Jaccard similarity metric | False positive error ($mm^2$) | False negative error ($mm^2$) |
|---|---|---|---|
| Superficial | 0.85 ± 0.12 | 0.013 ± 0.009 | 0.004 ± 0.003 |
| Intermediate | 0.82 ± 0.16 | 0.017 ± 0.012 | 0.004 ± 0.004 |
| Deep | 0.81 ± 0.16 | 0.019 ± 0.019 | 0.004 ± 0.003 |

Discussion

Automated quantification of nonperfusion using OCTA was improved using the image processing techniques

TABLE 1

Avascular area in diabetic retinopathy and control eyes

| | | mean ± SD ($mm^2$) | | | | |
|---|---|---|---|---|---|---|
| Plexus | ROI | Control (n = 13) | NPDR (n = 13) | p value[a] | Sensitivity, % (95% CI)[b] | AROC |
| Combined Inner retina | EAA | 0.00 ± 0.00 | 0.01 ± 0.04 | 0.168 | 26.9 (8.8-56.1) | 0.62 |
| | TAA | 0.15 ± 0.09 | 0.20 ± 0.10 | 0.121 | 7.7 (1.3-36.1) | 0.65 |
| Superficial | EAA | 0.00 ± 0.00 | 0.08 ± 0.09 | <0.001 | 91.9 (65.0-98.1) | 0.99 |
| | TAA | 0.16 ± 0.10 | 0.30 ± 0.17 | 0.007 | 25.4 (6.9-55.8) | 0.79 |
| Intermediate | EAA | 0.00 ± 0.00 | 0.01 ± 0.02 | 0.050 | 41.5 (17.1-70.0) | 0.69 |
| | TAA | 0.16 ± 0.10 | 0.23 ± 0.10 | 0.040 | 15.4 (2.4-45.5) | 0.71 |
| Deep | EAA | 0.00 ± 0.00 | 0.08 ± 0.13 | <0.001 | 78.1 (47.6-95.0) | 0.89 |
| | TAA | 0.15 ± 0.10 | 0.31 ± 0.22 | 0.022 | 23.1 (5.3-53.8) | 0.75 |
| Total of 3 plexuses | EAA | 0.00 ± 0.00 | 0.17 ± 0.23 | <0.001 | 94.6 (67.9-99.2) | 0.99 |
| | TAA | 0.46 ± 0.29 | 0.85 ± 0.47 | 0.017 | 23.1 (5.3-53.8) | 0.75 |

ROI, region of interest;
SD, standard deviation;
NPDR, non-proliferative diabetic retinopathy;
AROC, area under the receiver operating curve;
EAA, extrafoveal avascular area outside the central 1 mm circle;
TAA, total avascular area in the whole scan.
[a]Using Bonferroni correction for multiple analyses, the limit of false-positive error is 0.005.
[b]Sensitivity to detect NPDR with specificity held at 95% on the receiver operating curve.

described herein. PR-OCT allowed visualization of 3 distinct retinal plexuses and detection of capillary abnormalities that were not visible in inner retinal angiograms which combined the three plexuses. The vesselness filter effectively removed spurious pixels between vessels, and the use of the vessel-distance map improved characterization of vessel abnormality by minimizing the disproportionate contribution of large vessels and eliminating the undesirable classification of normal avascular area along large vessels of the superficial plexus as pathologic AA. The use of local reflectance signal strength to adjust thresholding minimized the detection of false positive nonperfusion areas and improved measurement repeatability. Morphologic operations further reduced false positive detection of AA.

By applying these techniques to eyes with mild NPDR, total nonperfusion area outside the central 1 mm circle could distinguish NPDR from control eyes with high diagnostic accuracy, even in eyes where combined inner retinal angiogram did not reveal any nonperfusion. This study confirms the potential of automatically quantified AA using OCTA as a biomarker in DR, even in cases where the disease is less severe.

The FAZ is known to have significant variability in normal and diabetic patients [36-38]. With segmentation into individual plexuses, the FAZ size can be further affected by segmentation scheme. Exclusion of the central 1 mm circle factored out this normal variation of FAZ and allowed good diagnostic accuracy of AA quantification.

In this cohort, the EAA was larger in the superficial and deep plexuses compared to the intermediate plexus, suggesting that nonperfusion occurs later in the intermediate plexuses in DR. A prospective study with a larger cohort can be conducted to verify this.

Example 2—Two-Level Distance Transform and Morphological Operations

FIG. 7 shows a pictorial representation of a two-level distance transform operation to generate a vessel distance map in accordance with the methods described herein. Starting with a binary vessel mask (FIG. 7A), denoising filters are applied at two different levels to produce two images with different amounts of noise removed (FIGS. 7B1 and 7B2). A distance transform is then applied to each of these denoised images to generate two different vessel distance maps (FIGS. 7C1 and 7C2). These two vessel distance maps are averaged to generate a single vessel distance map (FIG. 7D) for use in subsequent operations and calculations.

FIG. 8 shows a pictorial representation of the improvement conferred by using a two-level distance transformation to characterize areas of nonperfusion in ischemic and normal conditions. As shown in row Row A, when a level 1 distance transform is applied to the binary vessel mask of an ischemic eye, the proper result is obtained. However, the same level 1 scheme is used in a normal eye, a false area of nonperfusion is detected. Alternatively, as shown in Row B, when a level 2 distance transform is applied to the binary vessel mask of ischemic eye, the transformation fails to detect the nonperfusion area. The level 2 distance transform does properly characterize the normal eye as having no area of nonperfusion. Row C shows the effect of combing the level 1 and level 2 distance transforms for these cases and averaging the results. As shown, the combined two-level distance transform approach correctly characterizes both the ischemic and ischemic cases. Two-level distance overcomes the disadvantage that distance transform is sensitive to noise. Thus, the two-level distance transform approach is able to improve the sensitivity to ischemia while maintaining a high specifity to healthy subjects.

FIG. 9 shows a pictorial representation of an example set of thresholding and morphological operations that can be used to improve the quality of a nonperfusion map generated from a vessel distance map. Beginning with a vessel density map (FIG. 9A), the thresholding operation results in a binary image with a large number of spurious regions that overestimate nonperfusion area (FIG. 9B). In this specific example, there are numerous regions with a vessel distance less than 4 pixels (40 μm). An erosion operation using a 5-pixel wide kernel results in a pared binary image (FIG. 9C). This pared image is further filtered to reject regions having an area less than 8 pixels or a minor axis smaller than 2 pixels (FIG. 9D). A dilation operation is applied to the remaining regions using a 7-pixel-wide square kernel, and the resultant image (FIG. 9E) taken to be the final detected nonperfusion region.

Example 3—Optical Coherence Tomography Angiography Image Processing System

FIG. 10 schematically shows an example system 1000 for OCT image processing in accordance with various embodiments. System 1000 comprises an OCT system 1002 configured to acquire an OCT image comprising OCT interferograms and one or more processors or computing systems 1004 that are configured to implement the various processing routines described herein. OCT system 1000 can comprise an OCT system suitable for OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the methods depicted in FIGS. 1, 7, and 9 described above, can be implemented as a computer application, computer service, computer API, computer library, and/or other computer program product.

Figure 11:
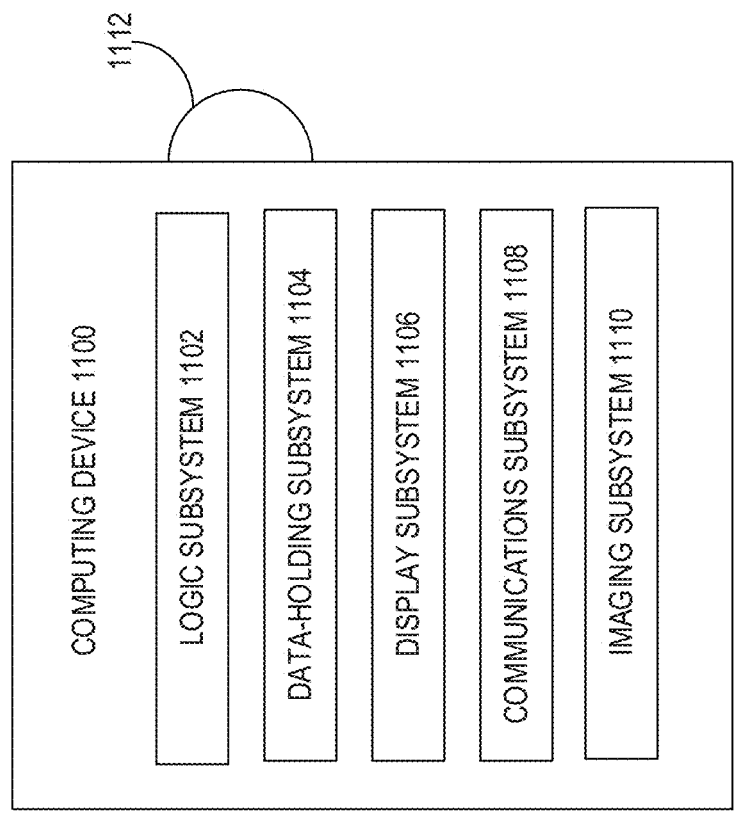
FIG. 11 schematically shows an example of a computing system in accordance with the disclosure.

FIG. 11 schematically shows a non-limiting computing device 1100 that can perform one or more of the above described methods and processes. For example, computing device 1100 can represent a processor included in system 1000 described above, and can be operatively coupled to, in communication with, or included in an OCT system or OCT image acquisition apparatus. Computing device 1100 is shown in simplified form. It is to be understood that virtually any computer architecture can be used without departing from the scope of this disclosure. In different embodiments, computing device 1100 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1100 includes a logic subsystem 1102 and a data-holding subsystem 1104. Computing device 1100 can optionally include a display subsystem 1106, a communication subsystem 1108, an imaging subsystem 1110, and/or other components not shown in FIG. 11. Computing device 1100 can also optionally include user input devices such as manually actuated buttons, switches, keyboards, mice, game controllers, cameras, microphones, and/or touch screens, for example.

Logic subsystem 1102 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1104 can include one or more physical, non-transitory, devices configured to hold data and/or instructions executable by the logic subsystem to implement the herein described methods and processes. When such methods and processes are implemented, the state of data-holding subsystem 1104 can be transformed (e.g., to hold different data).

Data-holding subsystem 1104 can include removable media and/or built-in devices. Data-holding subsystem 1104 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1104 can include devices with one or more of the following characteristics: volatile, nonvolatile, dynamic, static, read/write, read-only, random access, sequential access, location addressable, file addressable, and content addressable. In some embodiments, logic subsystem 1102 and data-holding subsystem 1104 can be integrated into one or more common devices, such as an application specific integrated circuit or a system on a chip.

FIG. 11 also shows an aspect of the data-holding subsystem in the form of removable computer-readable storage media 1112, which can be used to store and/or transfer data and/or instructions executable to implement the herein described methods and processes. Removable computer-readable storage media 1112 can take the form of CDs, DVDs, HD-DVDs, Blu-Ray Discs, EEPROMs, flash memory cards, USB storage devices, and/or floppy disks, among others.

When included, display subsystem 1106 can be used to present a visual representation of data held by data-holding subsystem 1104. As the herein described methods and processes change the data held by the data-holding subsystem, and thus transform the state of the data-holding subsystem, the state of display subsystem 1106 can likewise be transformed to visually represent changes in the underlying data. Display subsystem 1106 can include one or more display devices utilizing virtually any type of technology. Such display devices can be combined with logic subsystem 1102 and/or data-holding subsystem 1104 in a shared enclosure, or such display devices can be peripheral display devices.

When included, communication subsystem 1108 can be configured to communicatively couple computing device 1100 with one or more other computing devices. Communication subsystem 1108 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1100 to send and/or receive messages to and/or from other devices via a network such as the Internet.

When included, imaging subsystem 1110 can be used acquire and/or process any suitable image data from various sensors or imaging devices in communication with computing device 1100. For example, imaging subsystem 1110 can be configured to acquire OCT image data, e.g., interferograms, as part of an OCT system, e.g., OCT system 1002 described above. Imaging subsystem 1110 can be combined with logic subsystem 1102 and/or data-holding subsystem 1104 in a shared enclosure, or such imaging subsystems can comprise periphery imaging devices. Data received from the imaging subsystem can be held by data-holding subsystem 1104 and/or removable computer-readable storage media 1112, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A computer-based method of measuring nonperfusion in the retina, the method comprising:
   obtaining an optical coherence tomography (OCT) angiogram;
   thresholding the OCT angiogram, thereby generating a binary vessel mask, wherein thresholding the OCT angiogram comprises:

obtaining a structural OCT;
generating an en face reflectance image from the structural OCT;
filtering the en face reflectance image, thereby generating a reflectance-adjusted threshold image including respective reflectance-adjusted thresholds; and
thresholding the OCT angiogram using the respective reflectance-adjusted thresholds, thereby generating the binary vessel mask;
generating a vessel distance map from the binary vessel mask; and
generating a nonperfusion map from the vessel distance map.

2. The method of claim 1, wherein the OCT angiogram is a projection resolved OCT angiography (PR-OCTA) angiogram.

3. The method of claim 1, further comprising, prior to the thresholding, applying a vesselness filter to the OCT angiogram to enhance the vessel structure in the OCT angiogram.

4. The method of claim 3, wherein the vesselness fliter is a two-scale vesselness filter.

5. The method of claim 1, wherein the structural OCT comprises the ganglion cell layer (GCL) and inner plexiform layer (IPL).

6. The method of claim 5, wherein the thresholding the OCT angiogram using the reflectance-adjusted thresholds is performed according to:

$$B_{xy} = \begin{cases} 1, & \text{if } D_{xy} > T_{xy} \\ 0, & \text{if } D_{xy} < T_{xy} \end{cases};$$

wherein $B_{xy}$ is the binary vessel mask, $D_{xy}$ is the OCT angiogram, and $T_{xy}$ is the reflectance-adjusted threshold image.

7. The method of claim 1, wherein the filtering the en face reflectance image comprises:
calculating a logarithm of the en face reflectance image, thereby generating a log-transformed en face reflectance image;
applying a smoothing filter to the log-transformed en face reflectance image, thereby generating a smoothed log-transformed en face reflectance image;
scaling and offsetting the smoothed log-transformed en face reflectance image, thereby generating a scaled reflectance-adjusted threshold image; and
setting a maximum threshold in a region of the scaled reflectance-adjusted threshold image, thereby generating the reflectance-adjusted threshold image.

8. The method of claim 7, wherein the scaling and offsetting is performed according to:

$$T_{xy} = a \times G(S)_{xy} + b$$

wherein $T_{xy}$ is the reflectance-adjusted threshold image, G is a Gaussian operator, S corresponds to the log-transformed en face reflectance image, a is a scaling parameter, and b is an offset parameter.

9. The method of claim 7, wherein the smoothing filter is a Gaussian filter.

10. The method of claim 9, wherein the Gaussian filter is sized 15×15 pixels with a standard deviation of 8 pixels.

11. The method of claim 7, wherein the region of the scaled reflectance-adjusted threshold image is a foveal avascular zone (FAZ) region.

12. The method of claim 11, wherein the FAZ region comprises a 6 mm-diameter circular area centered on the FAZ.

13. The method of claim 1, wherein generating the vessel distance map from the binary vessel mask comprises:
denoising the binary vessel mask at a first level, thereby generating a first denoised binary mask image;
denoising the binary vessel mask at a second level, thereby generating a second denoised binary mask image;
applying a distance transform to the first denoised binary mask image, thereby generating a level-1 vessel distance map;
applying a distance transform to the second denoised binary mask image, thereby generating a level-2 vessel distance map; and
averaging the level-1 vessel distance map and level-2 vessel distance map, thereby generating the vessel distance map.

14. The method of claim 13, wherein the distance transform is a Euclidean distance transform calculated according to:

$$DT_{xy} = \min_{B_{x'y'}=1} \sqrt{(x-x')^2 + (y-y')^2}$$

wherein $DT_{xy}$ is the distance transform, (x, y) is a given pixel of the binary vessel mask, (x', y') corresponds to other pixels of the binary vessel mask, and $B_{x'y'}=1$ corresponds to pixels of the binary vessel mask that have a value to indicate a vessel.

15. The method of claim 1, wherein generating the nonperfusion map from the vessel distance map comprises:
thresholding the vessel distance map, thereby generating a first thresholded image;
eroding the first thresholded image, thereby generating a second thresholded image;
filtering the second thresholded image, thereby generating a third thresholded image; and
dilating the third thresholded image, thereby generating the nonperfusion map.

16. The method of claim 15, wherein the thresholding the vessel distance map is performed using a value of DT>4 when the vessel distance map is calculated according to:

$$DT_{xy} = \min_{B_{x'y'}=1} \sqrt{(x-x')^2 + (y-y')^2}$$

wherein $DT_{xy}$ is the distance transform, (x, y) is a given pixel of the binary vessel mask, (x', y') corresponds to other pixels of the binary vessel mask, and $B_{x'y'}=1$ corresponds to pixels of the binary vessel mask that have a value to indicate a vessel.

17. The method of claim 15, wherein the eroding the first thresholded image is performed using a 5-pixel wide square kernel.

18. The method of claim 15, wherein the filtering the second thresholded image comprises eliminating areas of the second thresholded image smaller than 8 pixels.

19. The method of claim 18, wherein the filtering the second thresholded image further comprises eliminating areas of the second thresholded image whose minor axis length is smaller than 2 pixels.

20. The method of claim 15, wherein the dilating the third thresholded image is performed using a 7-pixel wide square kernel.

21. A system for quantifying nonperfusion in the retina, comprising:
an OCT system to acquire an OCT angiogram of a sample;

a logic subsystem; and a data holding subsystem comprising machine-readable instructions stored thereon that are executable by the logic subsystem to:

threshold the OCT angiogram, thereby generating a binary vessel mask, wherein, to threshold the OCT angiogram, the logic subsystem is to:

obtain a structural OCT of the sample:

generate an en face reflectance image from the structural OCT;

filter the en face reflectance image, thereby generating a reflectance-adjusted threshold image including respective reflectance-adjusted thresholds; and threshold the OCT angiogram using the respective reflectance-adjusted thresholds, thereby generating the binary vessel mask;

generate a vessel distance map from the binary vessel mask; and generate a nonperfusion map from the vessel distance map.

22. The system of claim 21, wherein the OCT angiogram is a projection resolved OCT angiography (PR-OCTA) angiogram.

23. The system of claim 21, wherein the instructions are further executable by the logic subsystem to, prior to performing the thresholding, apply a vesselness filter to the OCT angiogram to enhance the vessel structure in the OCT angiogram.

24. The system of claim 21, wherein the structural OCT comprises the ganglion cell layer (GCL) and inner plexiform layer (IPL).

25. The system of claim 24, wherein, the logic subsystem is to threshold the OCT angiogram using the reflectance-adjusted thresholds according to:

$$B_{xy} = \begin{cases} 1, & \text{if } D_{xy} > T_{xy} \\ 0, & \text{if } D_{xy} < T_{xy} \end{cases};$$

wherein $B_{xy}$ is the binary vessel mask, $D_{xy}$ is the OCT angiogram, and $T_{xy}$ is the reflectance-adjusted threshold image.

26. The system of claim 21, wherein, to filter the en face reflectance image, the logic subsystem is to:

calculate a logarithm of the en face reflectance image, thereby generating a log-transformed en face reflectance image;

apply a smoothing filter to the log-transformed en face reflectance image, thereby generating a smoothed log-transformed en face reflectance image;

scale and offset the smoothed log-transformed en face reflectance image, thereby generating a scaled reflectance-adjusted threshold image; and set a maximum threshold in a region of the scaled reflectance-adjusted threshold image, thereby generating the reflectance-adjusted threshold image.

27. The system of claim 26, wherein the logic subsystem is to scale and offset the smoothed log-transformed en face reflectance image according to:

$$T_{xy} = a \times G(S)_{xy} + b$$

wherein $T_{xy}$ is the reflectance-adjusted threshold image, G is a Gaussian operator, S corresponds to the log-transformed en face reflectance image, a is a scaling parameter, and b is an offset parameter.

28. The system of claim 26, wherein the smoothing filter is a Gaussian filter sized 15×15 pixels with a standard deviation of 8 pixels.

29. The system of claim 26, wherein the region of the scaled reflectance-adjusted threshold image is a foveal avascular zone (FAZ) region.

30. The system of claim 29, wherein the FAZ region comprises a 6 mm-diameter circular area centered on the FAZ.

31. The system of claim 21, wherein, to generate the vessel distance map from the binary vessel mask, the logic subsystem is to:

denoise the binary vessel mask at a first level, thereby generating a first denoised binary mask image;

denoise the binary vessel mask at a second level, thereby generating a second denoised binary mask image;

apply a distance transform to the first denoised binary mask image, thereby generating a level-1 vessel distance map;

apply a distance transform to the second denoised binary mask image, thereby generating a level-2 vessel distance map; and average the level-1 vessel distance map and level-2 vessel distance map, thereby generating the vessel distance map.

32. The system of claim 31, wherein the distance transform is a Euclidean distance transform calculated according to:

$$DT_{xy} = \min_{B_{x'y'}=1} \sqrt{(x-x')^2 + (y-y')^2}$$

wherein $DT_{xy}$ is the distance transform, (x, y) is a given pixel of the binary vessel mask, (x', y') corresponds to other pixels of the binary vessel mask, and $B_{x'y'}=1$ corresponds to pixels of the binary vessel mask that have a value to indicate a vessel.

33. The system of claim 21, wherein, to generate the nonperfusion map from the vessel distance map, the logic subsystem is to:

threshold the vessel distance map, thereby generating a first thresholded image;

erode the first thresholded image, thereby generating a second thresholded image;

filter the second thresholded image, thereby generating a third thresholded image; and dilate the third thresholded image, thereby generating the nonperfusion map.

34. The system of claim 33, wherein the logic subsystem is to threshold the vessel distance map using distance transforms of the vessel distance map having a value greater than 4, and wherein the vessel distance map is calculated according to:

$$DT_{xy} = \min_{B_{x'y'}=1} \sqrt{(x-x')^2 + (y-y')^2}$$

wherein $DT_{xy}$ is the respective distance transform of the vessel distance map, (x, y) is a given pixel of the binary vessel mask, (x', y') corresponds to other pixels of the binary vessel mask, and $B_{x'y'}=1$ corresponds to pixels of the binary vessel mask that have a value to indicate a vessel.

35. The system of claim 34, wherein the first thresholded image is eroded using a 5-pixel wide square kernel;

wherein the second thresholded image is filtered by eliminating areas of the second thresholded image smaller than 8 pixels and eliminating areas of the second thresholded image whose minor axis length is smaller than 2 pixels; and wherein the third thresholded image is dilated using a 7-pixel wide square kernel.

36. A computer-based method of measuring nonperfusion in the retina, the method comprising:

obtaining an optical coherence tomography (OCT) angiogram;

thresholding the OCT angiogram, thereby generating a binary vessel mask; generating a vessel distance map from the binary vessel mask, wherein generating the vessel distance map from the binary vessel mask comprises:

denoising the binary vessel mask at a first level, thereby generating a first denoised binary mask image;

denoising the binary vessel mask at a second level, thereby generating a second denoised binary mask image;

applying a distance transform to the first denoised binary mask image, thereby generating a level-1 vessel distance map;

applying a distance transform to the second denoised binary mask image, thereby generating a level-2 vessel distance map; and averaging the level-1 vessel distance map and level-2 vessel distance map, thereby generating the vessel distance map; and generating a nonperfusion map from the vessel distance map.

37. The method of claim 36, wherein the distance transform is a Euclidean distance transform calculated according to:

$$DT_{xy} = \min_{B_{x'y'}=1} \sqrt{(x-x')^2+(y-y')^2}$$

wherein $DT_{xy}$ is the distance transform, (x, y) is a given pixel of the binary vessel mask, (x', y') corresponds to other pixels of the binary vessel mask, and $B_{x'y'}=1$ corresponds to pixels of the binary vessel mask that have a value to indicate a vessel.

* * * * *